United States Patent
Sundar Raj et al.

(10) Patent No.: US 9,314,753 B2
(45) Date of Patent: Apr. 19, 2016

(54) MULTI PLANE MIXER AND SEPARATOR (MPMS) SYSTEM

(71) Applicant: Stempeutics Research Private Limited, Bangalore (IN)

(72) Inventors: Swathi Sundar Raj, Bangalore (IN); Anish Sen Majumdar, Bangalore (IN); Nancy Priya, Bangalore (IN); Murali Cherat, Bangalore (IN); Prajod Thiruvambattil Lohidhakshan, Bangalore (IN); Manjunath Byalappa Sathya Kumar, Bangalore (IN)

(73) Assignee: Stempeutics Research Private Limited, Bangalore (IN)

( * ) Notice: Subject to any disclaimer, the term of this patent is extended or adjusted under 35 U.S.C. 154(b) by 0 days.

(21) Appl. No.: 14/423,925

(22) PCT Filed: Jul. 19, 2013

(86) PCT No.: PCT/IB2013/055938
§ 371 (c)(1),
(2) Date: Feb. 25, 2015

(87) PCT Pub. No.: WO2014/033564
PCT Pub. Date: Mar. 6, 2014

(65) Prior Publication Data
US 2015/0209742 A1    Jul. 30, 2015

(30) Foreign Application Priority Data
Aug. 27, 2012 (IN) .......................... 3514/CHE/2012

(51) Int. Cl.
*B01F 11/00* (2006.01)
*C07D 413/14* (2006.01)
(Continued)

(52) U.S. Cl.
CPC ......... *B01F 11/0028* (2013.01); *A61K 31/4245* (2013.01); *B01F 3/0807* (2013.01);
(Continued)

(58) Field of Classification Search
CPC ................... B01F 11/0028; B01F 2215/0073; C12M 45/02; G01N 1/38
USPC .................................................. 366/215–217
See application file for complete search history.

(56) References Cited

U.S. PATENT DOCUMENTS 760,664 A * 5/1904 Van Der Valk ............ B03B 5/02
209/43
1,871,374 A * 8/1932 John ........................ G03D 3/04
366/209
(Continued)

FOREIGN PATENT DOCUMENTS

FR     2219771 A1 * 9/1974 .......... B01F 11/0028
FR     2 952 312 A1    5/2011
(Continued)

*Primary Examiner* — Charles Cooley
(74) *Attorney, Agent, or Firm* — DLA Piper LLP (US)

(57) ABSTRACT

The present disclosure provides a multi plane mixer and separator (MPMS) system. The system comprises a base frame of predetermined shape configured to form a base for the MPMS system. A motor is mounted to the base frame for rotating the MPMS system. A ball joint mechanism is fixed to the motor using a link and other end of the ball joint mechanism is coupled to a fork. A container holding frame is connected to the fork using bars, wherein said container holding frame is capable of tilting up to 120° with respect to the base frame. And an MPMS container of predetermined shape detachably mounted on the container holding frame for mixing fluids of different density.

21 Claims, 7 Drawing Sheets

(51) Int. Cl.
  *A61K 31/4245* (2006.01)
  *C07D 413/10* (2006.01)
  *B01F 3/08* (2006.01)
  *B01F 15/00* (2006.01)
  *B01F 15/02* (2006.01)
  *C12M 1/33* (2006.01)
  *G01N 1/38* (2006.01)

(52) U.S. Cl.
  CPC ..... *B01F15/00331* (2013.01); *B01F 15/00389* (2013.01); *B01F 15/00396* (2013.01); *B01F 15/00538* (2013.01); *B01F 15/026* (2013.01); *C07D 413/10* (2013.01); *C07D 413/14* (2013.01); *C12M 45/02* (2013.01); *G01N 1/38* (2013.01); *B01F 2215/0073* (2013.01); *C07B 2200/13* (2013.01)

(56) References Cited

U.S. PATENT DOCUMENTS

| | | | | |
|---|---|---|---|---|
| 4,125,335 A * | 11/1978 | Blume | ........... | B01F 11/0028 241/175 |
| 4,702,610 A * | 10/1987 | Reynolds, Jr. | .... | B01F 15/00746 366/111 |
| 5,567,050 A * | 10/1996 | Zlobinsky | ........... | B01F 11/0008 366/110 |
| 5,639,160 A * | 6/1997 | Kishimoto | ......... | B01F 11/0028 366/208 |
| 5,921,676 A * | 7/1999 | Reynolds | ........... | B01F 11/0028 366/208 |
| 7,059,762 B2 * | 6/2006 | Yi | ................. | B01F 11/0005 366/208 |
| 7,101,077 B2 * | 9/2006 | Esteve | ............... | B01F 11/0028 366/110 |
| 7,448,789 B2 * | 11/2008 | Boquet | .............. | B01F 11/0028 366/110 |
| 7,578,612 B2 * | 8/2009 | Zhang | ............... | B01F 15/065 363/209 |
| 7,645,065 B2 * | 1/2010 | Bae | ..................... | B01F 11/0014 366/111 |
| 7,954,741 B2 * | 6/2011 | Kunc | ................ | B01F 11/0028 241/2 |
| 8,137,622 B2 * | 3/2012 | Li | ...................... | B01F 11/0028 366/111 |
| 2004/0151064 A1 * | 8/2004 | Yi | ..................... | B01F 11/0005 366/209 |
| 2005/0128863 A1 * | 6/2005 | Esteve | .............. | B01F 11/0028 366/110 |
| 2006/0193198 A1 * | 8/2006 | Bae | .................... | B01F 11/0014 366/111 |
| 2007/0064521 A1 * | 3/2007 | Miszenti | ........... | B01F 11/0028 366/208 |
| 2007/0154125 A1 * | 7/2007 | Boquet | .............. | B01F 11/0028 384/496 |
| 2009/0206187 A1 * | 8/2009 | Kunc | ................ | B01F 11/0028 241/66 |
| 2010/0190663 A1 * | 7/2010 | Li | ...................... | B01F 11/0028 506/33 |
| 2015/0004702 A1 * | 1/2015 | Raj | ..................... | C12M 45/02 435/378 |
| 2015/0209742 A1 * | 7/2015 | Sundar Raj | ....... | A61K 31/4245 435/303.3 |

FOREIGN PATENT DOCUMENTS

WO    WO 95/04591    2/1995
WO    WO 2005/012480 A2    2/2005

* cited by examiner

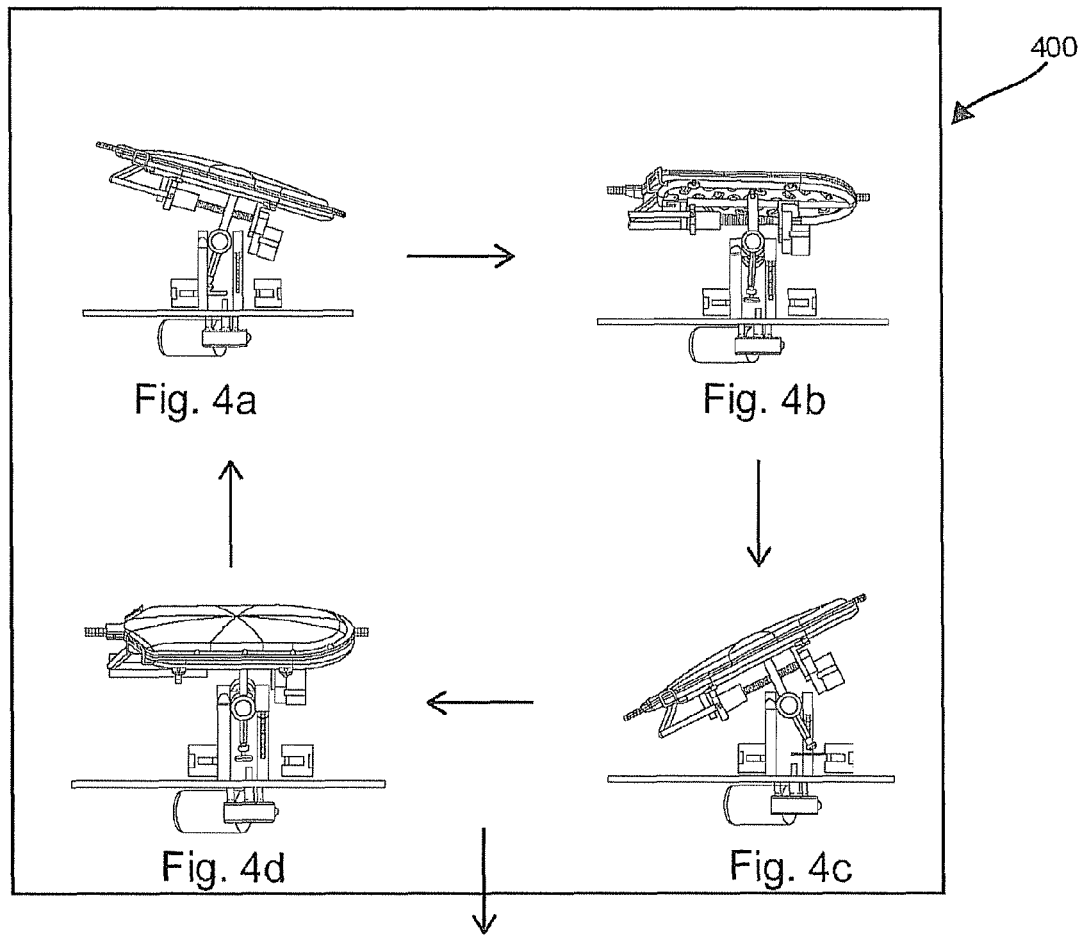
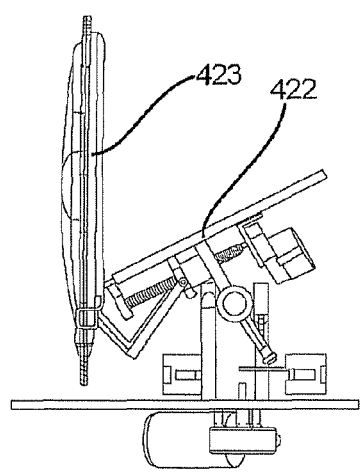

MULTI PLANE MIXER AND SEPARATOR (MPMS) SYSTEM

CROSS-REFERENCE TO RELATED APPLICATIONS

This application is a 35 USC §371 National Stage application of International Application No. PCT/IB2013/055938 filed Jul. 19, 2013, now pending; which claims the benefit under 35 USC §119(a) to India Application Serial No. 3514/CHE/2012 filed Aug. 27, 2012. The disclosure of each of the prior applications is considered part of and is incorporated by reference in the disclosure of this application.

TECHNICAL FIELD

Embodiments of the present disclosure relates to an agitator/mixer, more particularly embodiments relate to the multi plane mixer and separator system for mixing as well as for performing additional functions such as phase separation, sedimentation, despension etc.

BACKGROUND

Mixing involves manipulating a heterogeneous system to obtain a more homogenous system. Agitation is one of the means by which mixing can be accomplished. Mixing may result in change of heat and mass transfer. The equipment used for processes of mixing multiple liquids or solids make use of tanks/containers/flasks. The mixing process exerts certain amount of shear force on the matter being mixed.

Equipment used for mixing is referred to as mixers. The mixers differ in their construction based on the desired output and the limitations to be adhered to in obtaining the output. A mixer can generally disperse one phase (liquid, solid, gas) into a main continuous phase. A rotor or impellor, together with a stationary component known as a stator, is used either in a tank containing the solution to be mixed, or in a pipe through which the solution passes. The use of impellor or rotor creates shear force and thus acts as enabler for homogenization of two dissimilar materials. For example a high-shear mixer can be used to create emulsions, suspensions, lyosols (gas dispersed in liquid), and granular products. It is used in the adhesives, chemical, pharmaceutical, and plastics industries for emulsification, homogenization, particle size reduction, and dispersion.

Alternatively, a mixer can be provided with a stirrer connected to a motor to drive the stirrer for agitating the substances at required speeds. The stirrer could comprise a plurality of blades and is rotated in clock wise or anti clock wise direction using the motor for mixing liquid or solids. In conventional method the liquids of different densities are mixed by moving the liquids from top to bottom and vice versa thus the pattern of mixing the liquids is limited to only one pattern due to stirrer possessing only one degree of motion. In order to obtain uniform mixing, vigorous agitation is induced through high speed stirrers which will cause high turbulence and thus higher velocity of moving particles and shear force on the molecules.

Circulation and shear of the liquid in a vessel can be generated by certain combinations of pressure and vacuum. If mixing is to be done in the absence of pressure and vacuum, then satisfactory combination of vertical and lateral movement can be obtained economically using suitable dimension, proportions, and internal construction of liquid mixing vessels. This needs to be chosen to suit the demands of the application, for example, when liquids of different densities are required to be mixed homogeneously.

Various forms of mixers are also used in the biological lab and biotechnology industries, examples include vortex mixer. It consists of an electric motor with the drive shaft oriented vertically and attached to a cupped rubber piece mounted slightly off-center. As the motor runs the rubber piece oscillates rapidly in a circular motion. When a test tube or other appropriate container is pressed into the rubber cup and the motion is transmitted to the liquid inside and a vortex is created.

A magnetic stirrer or magnetic mixer is another example of a laboratory device that employs a rotating magnetic field to cause a stir bar immersed in a liquid to spin very quickly, thus stirring it. The rotating field may be created either by a rotating magnet or a set of stationary electromagnets, placed beneath the vessel with the liquid. Magnetic stirrers often include a hot plate or some other means for heating the liquid. Other such examples include homogenizers, orbital shakers etc.

Current mixers in the prior art are found to produce high velocity, turbulence, shear stress and frothing. All these factors can be damaging to biochemical/biological components and are therefore undesirable in biotechnology and biomedical industries. For example, several biochemical components such as proteins can get oxidized or denatured by frothing. Turbulence can be especially disadvantageous while mixing living biological samples such as cells and tissues which can be damaged by effect of shear force. Currently shear and turbulence effects can be reduced by using exogenous additives such as a mild surfactant. In biological samples use of such additives can be toxic and undesirable.

In light of the foregoing discussion, it is necessary to provide an improved system for efficient mixing. Present disclosure relates to a multi-purpose system for mixing at least two identical or different phases without any turbulence or frothing and can further also perform the functions of phase separation, sedimentation and dispersion as and when required after the mixing process.

SUMMARY OF THE DISCLOSURE

Embodiments of the present disclosure provides automated systems which can operate in multiple planes and perform multiple functions having additional advantages are provided through the provision of a system as claimed in the present disclosure.

Additional features and advantages are realized through the techniques of the present disclosure. Other embodiments and aspects of the disclosure are described in detail herein and are considered a part of the claimed disclosure.

One embodiment of the present disclosure provides an automated multi plane mixer and separator (MPMS) system which can perform multiple functions. The system comprises a base frame of predetermined shape configured to form a base for the MPMS system. A motor is mounted to the base frame for rotating the MPMS system. A ball joint mechanism is fixed to the motor using a link and other end of the ball joint mechanism is coupled to a fork. The fork is Y-shaped fork and one cross bearing is fixed on top ends of the limb of the fork. A container holding frame is connected to the fork using bars, wherein said container holding frame is capable of tilting up to 120° or to any user defined angle with respect to the base frame. Further, the system is provided with container or MPMS container of predetermined shape, which can be detachably mounted on the container holding frame.

In an embodiment of the present disclosure, a pair of bars are mounted on the base frame and at least one cross bearing cup is fixed to the top end of each bar using cross links, and the cross bearings on bars and fork forms universal joint.

In an embodiment of the present disclosure, at least one position sensor is provided on the ball joint mechanism to determine the position of the ball joint mechanism and the position sensor is interfaced with a controller.

In an embodiment of the present disclosure, a linear motion bearing with a bush bearing is coupled to the container holding frame using a linkage assembly to tilt the container holding frame up to 120° with respect to the base frame.

In an embodiment of the present disclosure, the linkage assembly comprises a pair of first link and a second link forming a revolute pair, and a motor, which is coupled to the linear motion bearing to selectively lift and lower the MPMS container, wherein the motor is interfaced with the controller.

In an embodiment of the present disclosure, at least one position sensor is provided on the container holding frame to control angle of lift of the agitation container, wherein the position sensor is interfaced with a controller.

In an embodiment of the present disclosure, the motor is interfaced with a controller, and speed and direction of rotation of the motor is controlled by the controller based on the requirement.

In an embodiment of the present disclosure, the MPMS container comprises a curved top surface and flat bottom surface, the flat bottom surface of the MPMS container comprises plurality of projections of predetermined shape and dimensions to facilitate uniform mixing of liquids in the MPMS container. The shape of the projections is at least one of triangle, square, rectangle, circular, ellipsoid and baffles.

In an embodiment of the present disclosure, the MPMS container comprises a semi-circular shaped inlet and a funnel shaped outlet and at least one valve interfaced with the controller to control the flow of matter into and out of the MPMS container.

In an embodiment of the present disclosure, the MPMS system is optionally enclosed in a chamber and the MPMS container is optionally made aseptic and preferably made aseptic for biological sample, and at least one temperature sensor, which is provided within the chamber to measure the temperature of the chamber, and the said temperature sensor is interfaced with the controller to maintain the temperature of the chamber within a predetermined limit. In situations where temperature sensor cannot come in contact with the mixing mediums, calibration method is used with a control circuit to manage desired temperatures.

In an embodiment of the present disclosure, the container holding frame rotates in both clockwise and anti-clock wise direction with the help of ball joint mechanism and control. It is also programmed to rotate along any plane.

In an embodiment of the present disclosure, the container holding frame can be programmed to rotate along any desired angle and plane.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE ACCOMPANYING FIGURES

The novel features and characteristic of the disclosure are set forth in the appended claims. The disclosure itself, however, as well as a preferred mode of use, further objectives and advantages thereof, will best be understood by reference to the following detailed description of an illustrative embodiment when read in conjunction with the accompanying figures. One or more embodiments are now described, by way of example only, with reference to the accompanying figures wherein like reference numerals represent like elements and in which:

FIGS. 4a to 4d illustrate various planar positions of the MPMS container to mix the liquids of different densities.

FIG. 4e illustrates the position of MPMS container when the container holding frame is titled to 90° with respect to base frame.

Figure 1A:
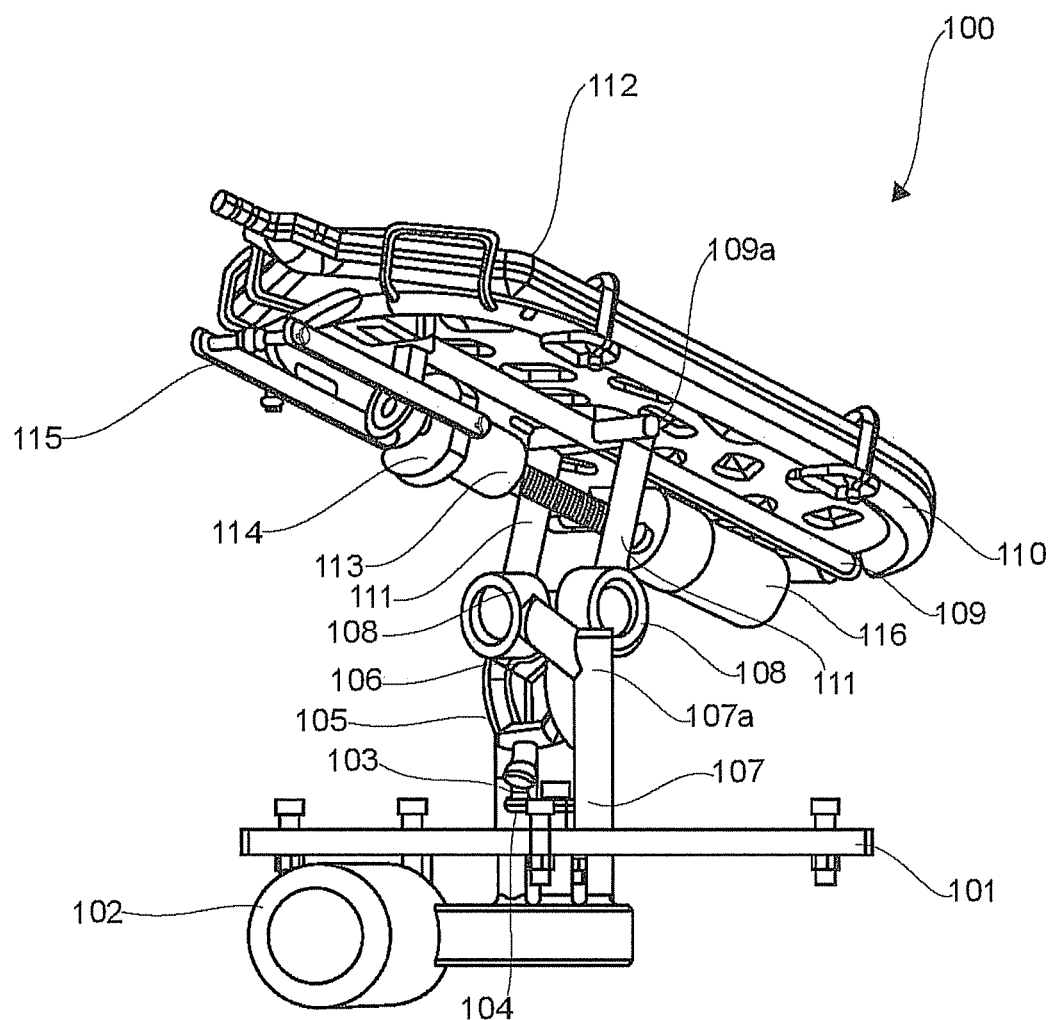
FIG. 1a illustrates perspective view of an MPMS system of the present disclosure.

The figures depict embodiments of the disclosure for purposes of illustration only. One skilled in the art will readily recognize from the following description that alternative embodiments of the structures and methods illustrated herein may be employed without departing from the principles of the disclosure described herein.

DETAILED DESCRIPTION

The embodiments of the present disclosure discloses an automated multi-plane mixer and separator (MPMS) system having a multiple utilities such as mixing, phase separation, sedimentation, dispension etc. as required after the mixing of the matter/content. This system can be used in any industries wherein mixing to two material/matter/component is required. More specifically this can be used where mixing of matter/components needs to be carried out without inducing turbulence and shear force. Few examples of industries where mixing of matter without turbulence and shear force is normally seen in biotechnology, biomedical and biochemical industries where live cells or biological samples are used or processed.

One of the application of MPMS system of present disclosure is in the biotechnology and biomedical industries wherein processing of biological samples is required. The processing of sample can be for various reasons such as sampling, testing, production of biological products, cell based products, isolation, culturing etc. wherein mixing or one of the functions of the MPMS system can be used effectively to get the desired output.

Biological sample can include biological tissue, cells and any other biological components. While, examples of biological tissues include but not limited to fat, placenta, synovial tissue, umbilical cord, cord blood, bone marrow, liver, pancreas etc.

The mixing of biological samples can be for various purposes which mostly does not required turbulence:

Different types of biological mixing that can be performed by the MPMS system includes but not limited to Uniform mixing of multiple miscible or immiscible liquids;

Dissolution of solute in solvent;

suspension of particulate solid in liquids;

washing of biological tissue with liquid buffer;

digestion/dissociation of biological tissues with liquid buffer containing digestive enzymes;

suspension of biological entities such as cells, viruses etc. in liquid buffer/medium;

mixing of micro particles or an affinity matrix such as antibody-coated beads for differential separation/selection/recovery/purification/clarification of specific/desired biological components such as growth factors, cytokines, proteins or cell populations from a liquid mixture or suspension.

The MPMS system of the present disclosure is designed to mix biological samples without turbulence while this system can be also used in case where turbulence is required.

Second functional aspect of the MPMS system is phase separation which includes but is not limited to:

Separation of multiple immiscible liquids mixture which has undergone physical and chemical interaction during mixing process. One such example would be separation of aqueous buffer fraction containing debris from fat tissue.

separation of biological tissues of different buoyant densities (e.g. fat and blood)

Third functional aspect of the device is sedimentation which includes but is not limited to:

sedimentation of cells from a suspension, that can include biological tissue such as bone marrow/cord blood or cells suspended in culture medium/buffer/other agents known in art.

sedimentation of micro particle/affinity matrix complexes for selection/recovery/purification/clarification of specific/desired biological components such as growth factors, cytokines, proteins or cell populations from a liquid mixture or suspension. E.g. blood, bone marrow, umbilical cord or digested tissue.

Fourth functional aspect includes dispension wherein uniform dispension of cells/solids/micro particles etc. into different containers of defined volumes is required.

The foregoing has broadly outlined the features and technical advantages of the present disclosure in order that the detailed description of the disclosure that follows may be better understood. Additional features and advantages of the disclosure will be described hereinafter which form the subject of the claims of the disclosure. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope of the disclosure as set forth in the appended claims. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

This disclosure is drawn, inter-alia, to an MPMS system, more particularly relates to the MPMS system used to mix liquids of different densities.

Figure 1B:
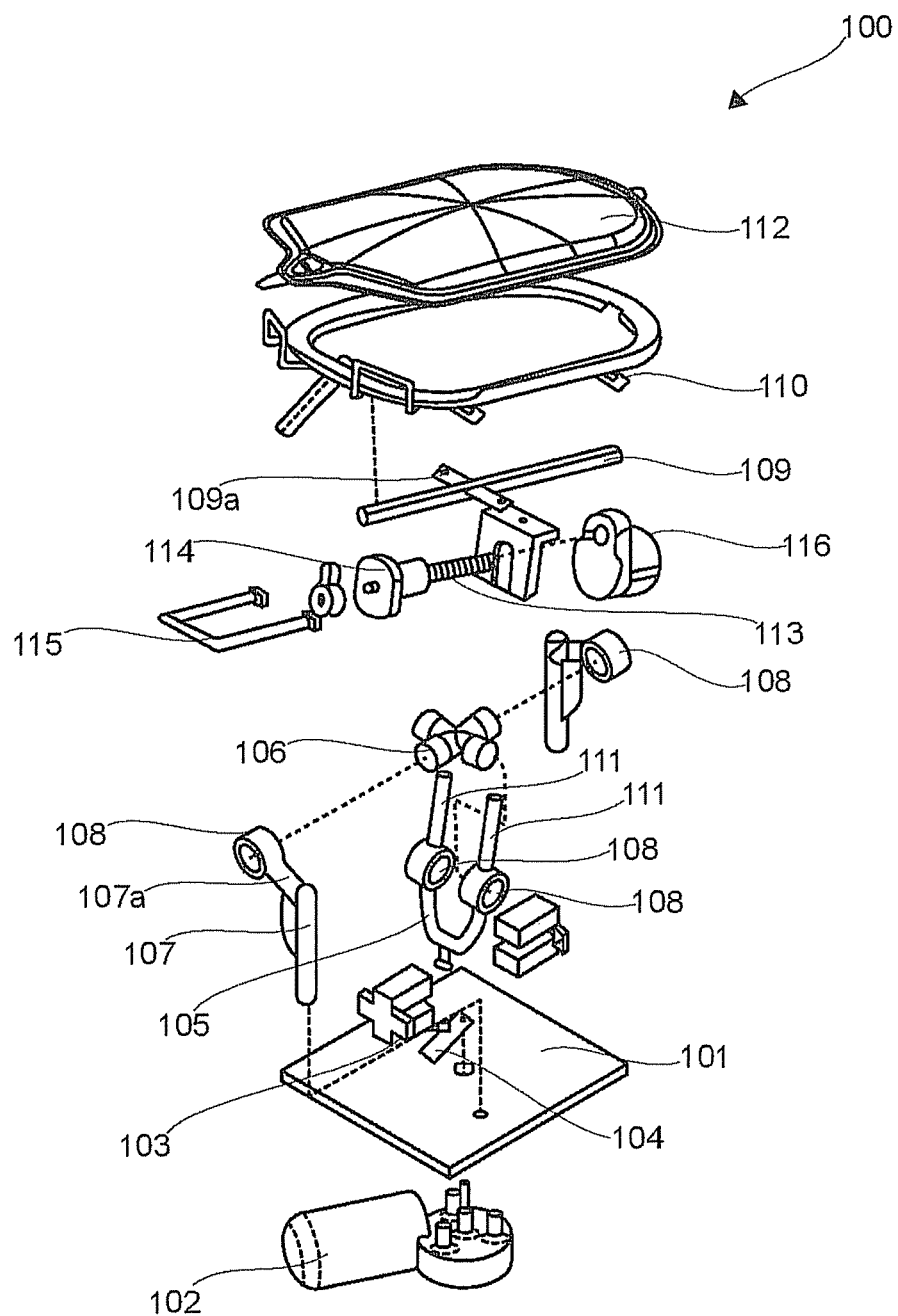
FIG. 1b illustrates magnified and exploded view of an MPMS system.

FIGS. 1a and 1b are exemplary embodiments of the present disclosure illustrating perspective view and exploded view of the MPMS system (100). The system (100) comprises a base frame (101) of predetermined shape configured to form base of the system (100). The base frame (101) can be made from any material selected from group comprising but not limited to metal and non-metal. A first motor (102) is mounted to the base frame (101) of the MPMS system (100) for rotating the MPMS system (100) to bring about mixing. The first motor (102) is preferably a DC motor to change the speed by modulating the voltage or current. The Rotation per Minute (RPM) of the first motor (102) is defined by desired mixing velocity. The system is provided with a ball joint mechanism (103), one end of which is fixed to the first motor (102) through an adjustable link (104), and other end of the ball joint mechanism (103) is fixed to a fork (105). The adjustable link (104) can be varied in the scale range of 0-30 mm as per the required angle of mixing. The ball joint mechanism (103) comprises a ball and socket joint, this ball joint mechanism (103) provides a sliding fit that helps to generate multi-planar motion. The fork (105) is a Y-shaped fork and—one cross bearing cup (108) is coupled to each top end of the fork (105) to obtain specified angular motion of the MPMS system (100). Further, the system (100) comprises a pair of bars/pillars (107) mounted on the base frame (101) and at least one cross bearing cup (108) is fixed to top end of each bar (107) using cross links (107a). A cross bearing (106) is encompassed in the cross bearing cups (108) that is coupled to fork (105) and lower bars/pillars (107) to form universal joint to transfer planar motion of ball joint mechanism into multi-planar motion to rotate the MPMS system (100) for mixing.

A container holding frame (110) is pivoted on a cross link (109), and said cross link (109) is connected to Y-shaped fork (105) using upper bars/pillar (111) through a connecting member (109a) for holding the MPMS container (112). The container holding frame (110) is configured to tilt up to 120° further, the angle can be modified as per user requirements with respect to the base frame (101). In one of the embodiment wherein the phase separation process is required after mixing, the container holding frame (110) can be to tilt to 90°. The system (100) is provided with a container referred to as MPMS container (112). The MPMS container (112) is of predetermined shape detachably mounted on the container holding frame (111) for mixing.

In an embodiment of the present disclosure, the first motor (102) is interfaced with a controller (218) (see FIG. 2) to control speed and direction of rotation of the first motor (102) based on the requirement. The speed and direction of the first motor (102) is defined by the mixing velocity. The container holding frame (110) can be rotated in both clock-wise and anti-clock wise direction and is controlled by the Controller (218).

Figure 2:
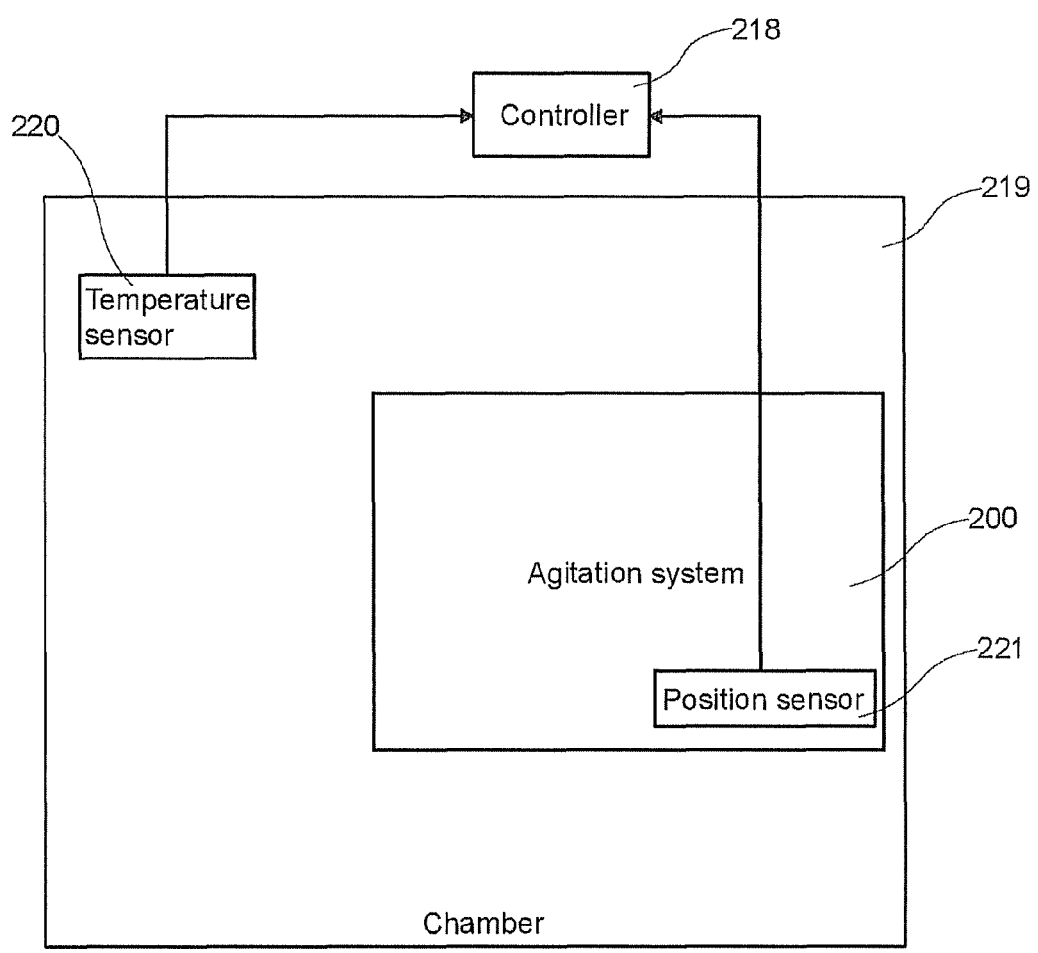
FIG. 2 illustrates block diagram of MPMS system enclosed in a chamber.

Further, the MPMS system (100) comprises a liner motion bearing (113) with a bush bearing (114) coupled to the container holding frame (110) using a linkage assembly (115) to tilt the container holding frame (110) up to 90° with respect to the base frame (101). The linkage assembly (115) comprises a pair of first links and second links forming a revolute pair. The linear motion bearing (113) is coupled to a second motor (116) to selectively lift and lower the MPMS container (112). Further, at least one position sensor (221) as shown in FIG. 2 is provided on the container holding frame (110) to control angle of lift of the MPMS container (112). In an embodiment of the present disclosure, the second motor (116) and the position sensors (221) are interfaced with the controller (218) as shown in FIG. 2.

In an embodiment of the present disclosure, the container holding frame (110) is configured to tilt up to 120° with respect to the base frame (101). To achieve 120° titling of the container holding frame (110) a longer lead screw, a second motor (116) with higher torque and power rating, linkage assembly (115) of different dimensions are configured in the MPMS system (100). The 120° titling of the container holding frame (110) is used in the foregoing applications including but not limited to fractional distillation and partial phase separation to tap various liquids from multiple drain ports of the MPMS container (112).

In one embodiment of the present disclosure, the MPMS container (112) has a locking means for locking the MPMS container (112) to the container holding frame (110). Locking can be through any suitable locking mechanism, and in one aspect of the present disclosure, the MPMS container (112) contains a side rib and the J-Clamp to lock the MPMS container (112) with the container holding frame (110) with a spring force.

FIG. 2 is an exemplary embodiment of the present disclosure which illustrates block diagram of MPMS system (200). The MPMS system (200) is enclosed in a chamber (219) in a conditioned environment At least one temperature sensor (220) is provided with in the chamber (219) to measure the temperature in the chamber (219), and said temperature sensor (220) is interfaced with the controller (218) to control the temperature in the in the chamber (219) within a predetermined limit. In one of the embodiment of the present disclosure, the chamber (219) is maintained at 37° C. by suitable means selected from a group comprising but not limited to warm air circulation, or use of infra-red, heating mechanism or other known in the art.

Figure 3A:
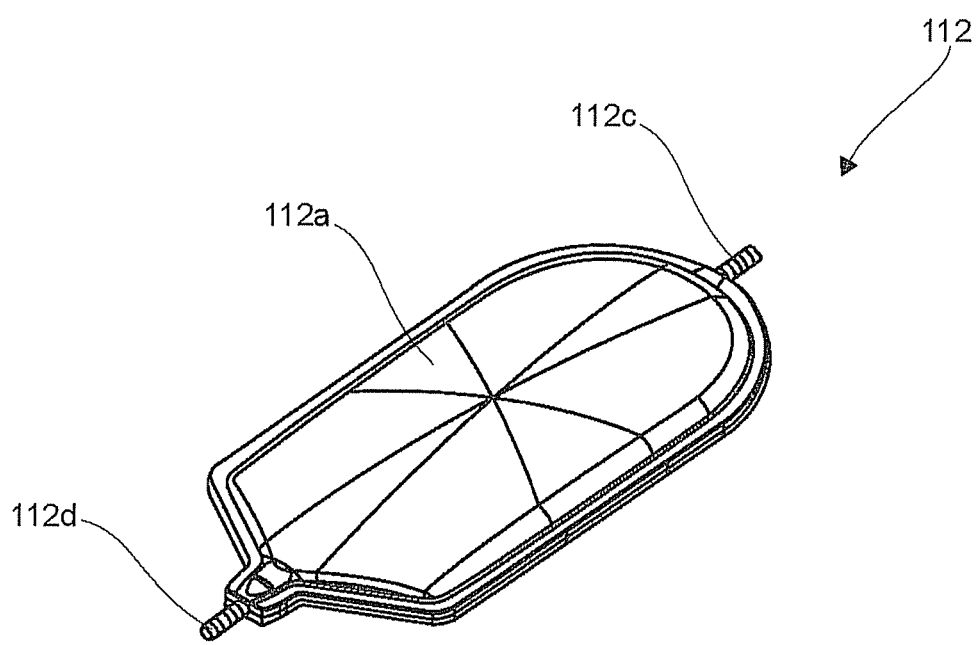
FIGS. 3a and 3b illustrates perspective view and bottom view of the MPMS container of the present disclosure.
Figure 3B:
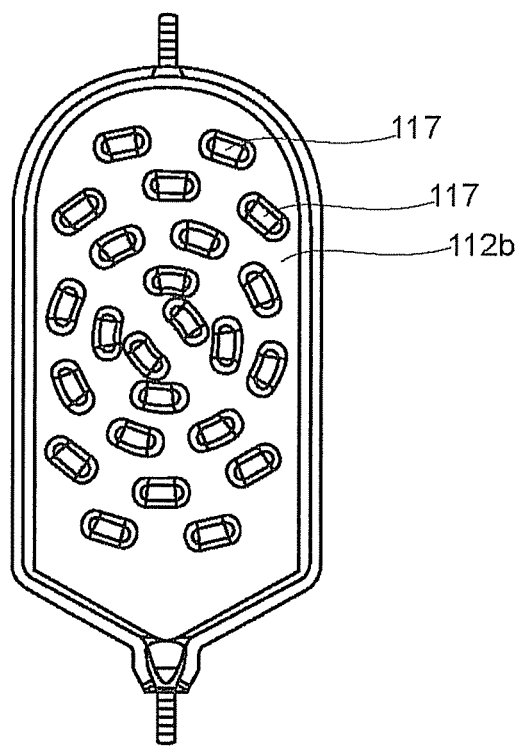
Figure 3C:
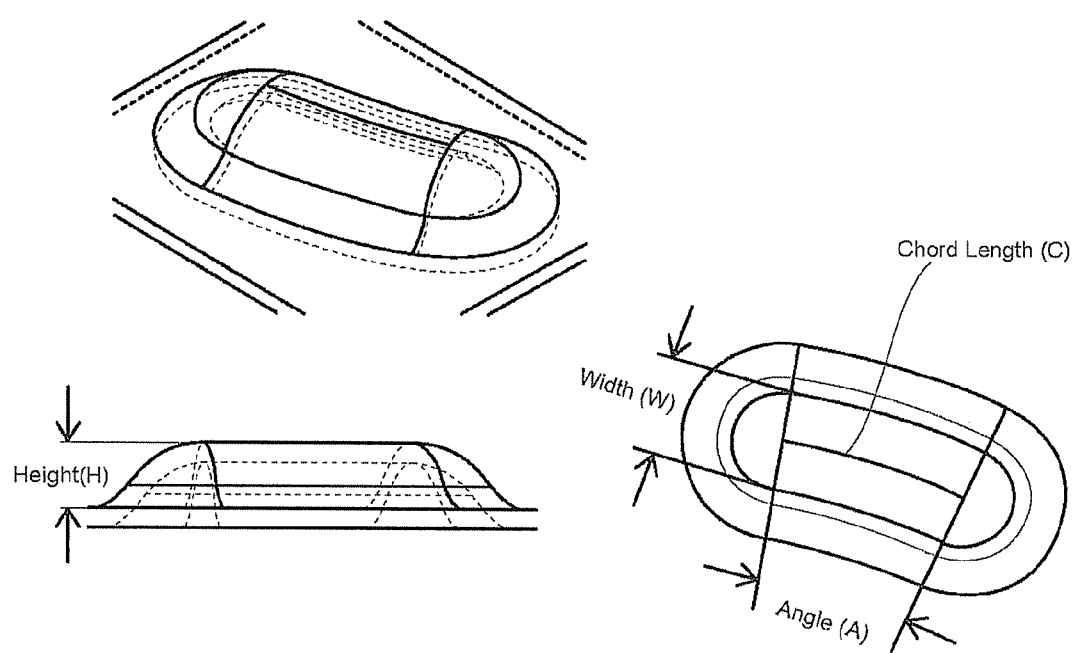
FIG. 3c illustrates various views of projections provided in bottom plate of the MPMS container of the present disclosure.

FIGS. 3a and 3b are exemplary embodiments of the present disclosure illustrating perspective view and bottom view of the MPMS container (112). The MPMS container (112) comprises a curved top surface (112a) and flat bottom surface (112b). The flat bottom surface (112b) of the MPMS container comprises plurality of projections (117) in predetermined profile arranged in predetermined pattern to facilitate homogenous mixing without generating turbulence or shear force. The projections (117) (shown in FIG. 3c) slow down the velocity of the liquid in the container (112) and lamellar flow motion will be maintained. The dimensions, distance, angle and pattern of arrangement of the projections improves the homogenous mixing of the fluids. The dimensions, distance, angle of the projections (117) along with the pattern of arrangement of the projections (117) will vary based on requirement and application to facilitate homogenous mixing.

In an embodiment of the present disclosure, shape of the projections (117) (shown in FIG. 3c) is selected from group comprising but not limited to triangle, square, rectangle, circular, ellipsoid and baffles. The MPMS container (112) further comprises a semi-circular shaped inlet (112c) and a funnel shaped outlet (112d) at either ends of the MPMS container (112). The inlet (112c) is configured to receive the input/material into the MPMS container (112) for mixing and the outlet (112d) to deliver the output for further processing. In an embodiment of the present disclosure, the semicircular portion provided at inlet of the MPMS container (112) will facilitate laminar flow. The funnel shaped portion provided at outlet of the MPMS container (112) allow effective phase separation. In another embodiment the outlet can be of other shapes including but not limited to semicircular, ellipsoidal, rectangular etc. Inlet and outlet valves are controlled by pinch valves.

The MPMS container (112) can be made from any material selected from a group comprising but not limited to non-metal and metal. In one of the embodiment of the present disclosure, MPMS container (112) is made from a rigid plastic such as polypropylene or polystyrene. The MPMS container (112) is optionally made aseptic. The MPMS container (112) is preferably made aseptic for biological tissues. The dimension of the MPMS container (112) depends on the application.

As an example the below table 1 illustrates various ratios of the dimensions of the MPMS container (112). However, the dimensions provide in the table 1 is for an illustration purpose and should not be construed as limitation of MPMS. The dimension of the container can be varied depending on the requirement.

TABLE 1

| Length of the container in (mm) | Width of the container in (mm) | Height of the container in (mm) | Volume of the container in (ML) |
| --- | --- | --- | --- |
| 420 | 160 | 35 | 1200 |
| 400 | 150 | 35 | 970 |
| 365 | 135 | 35 | 730 |
| 335 | 115 | 35 | 520 |
| 280 | 90 | 35 | 300 |

FIGS. 4a to 4d are exemplary embodiments of the present disclosure illustrating various planar positions of the MPMS system (400) during mixing.

Planar Movement:

The MPMS system (100) of FIG. 1 will be rotated by the first motor (102). The first motor (102) will rotate the ball joint mechanism (103) through the link (104). The ball and socket in the ball joint mechanism (103) will make sliding fit which helps to transfer planar motion into multi-planar motion. The fork (105) connected to the ball joint mechanism (103) comprises of cross bearing cups (108) on its top ends to accommodate the cross bearing (106) by making a universal joint with cross bearing cups (108) mounted on lower bars/pillars (107) to transfer the rotation motion from motor to the container holding frame (110) through upper pillar/bars (111), which is joined to the cross bearing cups (108) of the fork (105). The fork (105) makes multi planar motion when the ball joint mechanism (103) makes planar motion. The MPMS container (112) mounted on container holding frame (110) will be rotated in various planar positions for various mixing results. FIGS. 4a to 4d illustrates the system 400 in different planner motions.

FIG. 4e is an exemplary embodiment of the present disclosure which illustrates perspective view of MPMS container (112) of FIG. 1 during phase separation. After the process of mixing, where required the controller (218) (shown in FIG. 2) will activate the agitation lift motor (116) also called a second motor, the second motor (116) will rotate the linear motion bearing (113). The bush bearing (114) which is connected to an end of the linear motion bearing (113) will push the linkage assembly (115). The linkage assembly (115) acting as revolute pair will lift the container holding frame (110) vertically up to 90° with respect to base frame (101) for phase separation. The position sensors (422) (as shown in FIG. 4e) provided on the container holding frame (110) will be interfaced with the controller (218). The position sensors (422) will determine the position of the container holding frame (110), once the desired position is reached the controller (218) will stop the agitation lift motor (116). The exemplary illustration of phase separation is shown in the FIG. 4e.

In one aspect of the present disclosure, the MPMS system (100) works on the principle of—CAM and rotary joint mechanism. The MPMS system (100) works on a single pivot agitation mechanism with motor driven by CAM mechanism. The MPMS container (112) is held on collar and bush assembly along the X-axis to perform semi-rotary motion through a motor (102), and the MPMS container (112) is mounted on inclined plane for swivel and rotary motion.

Example:

The working of MPMS system is explained with the help of example. However, this example should not be construed as limitation of the MPMS system. In this example the MPMS system is used to process—biological samples. However, the same MPMS system can be used for processing non-biological samples also.

The MPMS system can be used in Stromal Vascular Fraction (SVF) processing device (500) for mixing the tissue with different buffer solution and agitating the mixture followed by phase separation of fatty upper layer from aqueous lower layer.

Figure 5:
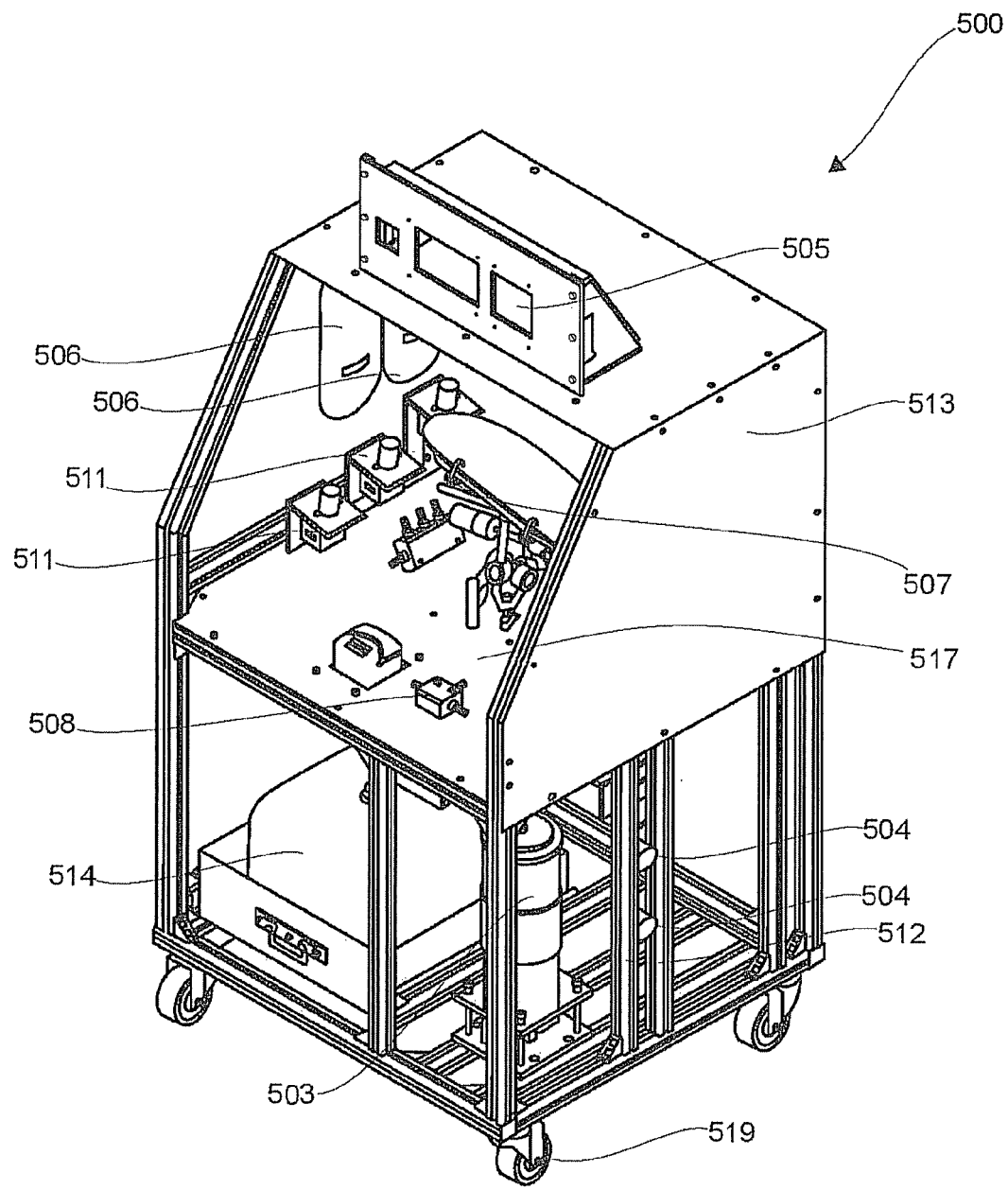
FIG. 5 illustrates Stromal Vascular Fraction (SVF) processing device associated with MPMS system of the present disclosure.

FIG. 5 illustrates the Stromal Vascular Fraction (SVF) processing device (500) associated with MPMS system (501) of the present disclosure. The SVF processing device (500) comprises of chamber (517) or cover of suitable design, the chamber (517) can be transparent or opaque. The chamber (517) is provided with a user interface having LCD display (505) and input buttons to feed in required parameter for processing the sample. The interface (505) is very user friendly and programmed for adjusting the setting of the device.

The SVF processing device (500), comprising of buffer and enzymes containers/units (506), MPMS system (100) and cell concentration unit (503). The geometry of the chambers/units can vary but not limited to cubical, square, rectangular, cylindrical and other known geometry which can be used for the purpose. The MPMS system (100), also referred as tissue processing unit is attached to a rotating/agitation mechanism/MPMS assembly. The device is also provided with one or two peristaltic pump (512) to feed in the lipoaspirated tissue sample collected from the patient for processing into the MPMS system (100) and to drain the liquids after phase separation. This chamber/unit (517) is made of rigid or semi rigid non-reactive plastic or materials similar in physiochemical composition like poly vinyl, polycarbonate but not limited.

The tissue samples obtained from surgery is transferred into the MPMS system (100)/tissue processing unit, to provide maximum flexibility to surgeons using various commercially available liposuction instruments, the inlet tubing into tissue processing unit is designed to accept various liposuction containers currently in use for such surgical procedures. This inlet tubing is connected to the device via tubing and adaptors and the sample is then pumped into the MPMS system (100) using the peristaltic pump (512) for washing and digestion. The sterile, disposable containers (506) are used for housing wash buffers and buffers containing digestive enzymes. These containers (506) are provided with pre-designed outlets and are connected to the pinch valve (511) using appropriate tubing during normal operation. The each container (506) are configured to hold predetermined quantity liquid, ranging from about 0.5 liters to about 10 liters. The next operation in this sequence is to pump in a predetermined volume of buffer, from one of the buffer containers (506) using the peristaltic pump (512) but by activating a second valve in the-pinch value controller. Predetermined volume is an amount equal to the amount of fat tissue that is being processed. The volume is calculated based on the tube diameter and time, and is fed into the user-interface (511) electronic circuitry using the data input keyboard. Once the desired volume is achieved, then the pumping is stopped.

The MPMS container (112) is then agitated for a period of 2-15 min by energizing the motor arm of the MPMS system (100). The motorized arm, connected to the motor is designed to deliver a uniform pitch and amplitude to enable thorough mixing of the samples. After the mixing, the MPMS container (112) is tilted to a vertical position and allowed to rest for a period of 2-15 min and the two phases begin to separate (the fat-enriched upper phase and the lower aqueous phase are clearly discernible). A predetermined volume of the lower aqueous phase, usually 95% of the initial input volume of buffer, is drained by activating the outlet port and valve, and the wash solution is collected in the waste reservoir. Draining through a filter (or mesh of 100-200 micron) ensures that the fat enriched layer is not drained out at this step. This wash step is repeated for 3-4 times for complete removal of blood cells from the tissue.

The digestion phase of the process commences with the addition of an equal volume of buffer containing collagenase, or a combination of collagenase, pepsin, trypin, papain or similar proteolytic enzyme pre-warmed to certain limit. The enzyme/buffer solution from one of two containers is pumped through the third valve in the pinch valve using the peristaltic pump.

The clamp fixtures that hold the MPMS container (112) in place is equipped with a thermal pad, that, when energized warms up the contents of the MPMS container (112). The thermal control mechanism has been calibrated to thoroughly and evenly heat the interior of the liquid to 37° c. A sensor coupled to a (temperature controller) maintains the constant temperature throughout the digestion process. To increase the efficiency and uniformity of digestion, the motorized arm is activated to deliver a gentle but thorough mixing of the enzyme with the fat tissue throughout this process. Based on the tissue volume and the enzyme concentration used, a minimum of 30-60 min of digestion with continuous mixing is carried out. At the end of the digestion process, a pre-calculated volume of—serum is pumped using the same liquid-handling circuitry used for delivering the enzyme/buffer mix to inactivate the enzyme. In another embodiment an enzyme inhibitor, not limited to EGTA or similar chemically-defined inhibitor is added to inactivate the enzyme. In yet another embodiment the enzyme is not inactivated as the extensive washing of the digested cells is sufficient to completely remove the enzyme. Finally, the motorized arm is brought to rest, followed by shutting off of the thermal pad and the module is allowed to rest for 2-10 min. Then, the MPMS container (112) is tilted up-to 90° with respect to the base frame for the phase separation between fatty and aqueous fractions to take place. After the phase separation process the wash solutions are drained into the waste container (514) using a prefabricated outlet—controlled by a valve with a unidirectional flow (inside to outside) is used to drain. And the cell slurry from the MPMS system (100) is fed into the cell concentration unit/assembly (503) through the outlet—for further processing.

The cell concentration unit/assembly (503) is selected from group comprising but not limited to simple filtration, pressure assisted filtration, and vacuum assisted filtration or combination thereof. The cell concentration unit/assembly (507) is optionally housed with a drive mechanism that enables controlled rotation of the chamber. The drive mechanism is either magnetic, mechanical, electromechanical or a combination thereof. The design and construction of the chamber also incorporates a vibratory mechanism to dislodge cells and debris that clog the filters. Either by itself, or in combination, these mechanisms improve flow rate and prevent clogging of filter materials and enable cell concentration.

The example provided above is just for illustration purpose; however the MPMS system can be used for mixing the non-biological samples including but not limited to any liquids, liquids and solids etc.

Equivalents

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERRAL NUMERALS

| Reference Number | Description |
| --- | --- |
| 100 | Multi Planar Mixing and Separation system |
| 101 | Base frame |
| 102 | First Motor |
| 103 | Ball joint mechanism |
| 104 | Link |
| 105 | Fork |
| 106 | Cross bearing |
| 107 | Lower Bars/pillars |
| 107a | Cross links on lower pillars |
| 108 | Cross bearing cups |
| 109 | Cross link |
| 109a | Connecting member |
| 110 | Container holding frame |
| 111 | Upper Bars/pillars |
| 112 | MPMS container |
| 112a | Top surface of the MPMS container |
| 112b | Bottom surface of the MPMS container |
| 112c | Inlet of the MPMS container |
| 112d | Outlet of the MPMS container |
| 113 | Linear motion bearing |
| 114 | Bush bearing |
| 115 | Linkage assembly |
| 116 | Second motor |
| 117 | Projections |
| 218 | Controller |
| 219 | Chamber |
| 220 | Temperature sensor |
| 221 | Position sensor on ball joint mechanism |
| 422 | Position sensor on container holding frame |
| 423 | Heating pads |
| 500 | SVF processing device |
| 503 | Cell concentration unit |
| 505 | User interface |
| 506 | Buffer and enzyme container |
| 507 | Heater |
| 508 | 3 way manifold |
| 511 | Pinch valve |
| 512 | Peristaltic pump |
| 513 | Frame |
| 514 | Waste collector |
| 517 | Chamber |
| 519 | Castor wheels |

The invention claimed is:

1. A Multi Planar Mixer and Separator (MPMS) system (100) comprising:
a base frame (101) of predetermined shape configured to form a base of the MPMS system (100);
a first motor (102) mounted to the base frame (101) for rotating the MPMS system (100);
a ball joint mechanism (103), wherein one end of said ball joint mechanism (103) is fixed to the motor (102) using a link (104), and other end of the ball joint mechanism (103) is coupled to a fork (105);
a container holding frame (110) connected to the fork (105) using bars (111), wherein said container holding frame (110) is capable of tilting up to 120° with respect to the base frame (101); and
an MPMS container (112) of predetermined shape detachably mounted on the container holding frame (110) for mixing liquids of different density.

2. The system as claimed in claim 1, wherein the fork (105) is Y-shaped fork and cross bearing cups (108) are fixed on top ends of the fork (105).

3. The system as claimed in claim 2, wherein cross bearings (106) are encompassed in the cross bearing cups (108) to form a universal joint.

4. The system as claimed in claim 1, wherein a pair of bars (107) are mounted on the base frame (101) and at least one cross bearing cup (108) is fixed to top end of each bar using cross links (107a).

5. The system as claimed in claim 4, wherein the cross bearings (106) are encompassed in the at least one cross bearing cup (108) to form a universal joint.

6. The system as claimed in claim 1 comprises at least one position sensor (221) provided on the ball joint mechanism (103) to determine the position of the ball joint mechanism (103), wherein the position sensor (221) is interfaced with a controller (118).

7. The system as claimed in claim 1 comprises a linear motion bearing (113) with a bush bearing (114), which is coupled to the container holding frame (110) using a linkage assembly (115) to tilt the container holding frame (110) up to 120° with respect to the base frame (101).

8. The system as claimed in claim 7, wherein the linkage assembly (115) comprises a pair of first links and second links forming a revolute pair.

9. The system as claimed in claim 7 comprises a second motor (116) coupled to the linear motion bearing (113) to selectively lift and lower the MPMS container (112), wherein the second motor (116) is interfaced with a controller (218).

10. The system as claimed in claim 1 comprises at least one position sensor (221) provided on the container holding frame (110) to control angle of lift of the MPMS container (112), wherein the position sensor (221) is interfaced with a controller (218).

11. The system as claimed in claim 1, wherein the motor (102) is interfaced with a controller (218), and speed and direction of rotation of the motor (102) is controlled by the controller (218).

12. The system as claimed in claim 1, wherein the MPMS container (112) comprises a curved top surface (112a) and flat bottom surface (112b).

13. The system as claimed in claim 12, wherein the flat bottom surface (112b) of the MPMS container (112) comprises plurality of projections (117) of predetermined profile arranged in predetermined pattern to facilitate uniform mixing fluids without turbulence and shear stress in the MPMS container (112).

14. The system as claimed in claim 13, wherein the shape of the projections (117) is at least one of triangle, square, rectangle, circular, and ellipsoid.

15. The system as claimed in claim 1, wherein the MPMS container (112) comprises a semi-circular shaped inlet (112c) and a funnel shaped outlet (112d).

16. The system as claimed in claim 15 comprises at least one valve interfaced with a controller (218) to control the flow of liquids into the MPMS container (112).

17. The system as claimed in claim 1, wherein the MPMS container (112) is made aseptic.

18. The system as claimed in claim 1, wherein the MPMS system (100) is enclosed in a chamber (219).

19. The system as claimed in claim 18 comprises at least one temperature sensor (220), provided within the chamber (219) to measure the temperature in the chamber (219), and the temperature sensor (220) is interfaced with a controller (218) to maintain the temperature of the chamber (219) within a predetermined limit.

20. The system as claimed in claim 1, wherein the container holding frame (110) rotates in both clockwise and anti-clockwise direction with the help of the first motor (102) and ball joint mechanism (103).

21. The system as claimed in claim 1, wherein the liquids are biological samples including biological tissue, cells or any other biological components and non-biological samples.

* * * * *